United States Patent
Hautvast (10) Patent No.: US 9,161,724 B2
(45) Date of Patent: Oct. 20, 2015

(54) MULTI-CARDIAC SOUND GATED IMAGING AND POST-PROCESSING OF IMAGING DATA BASED ON CARDIAC SOUND

(75) Inventor: Guillaume Leopold Theodorus Frederik Hautvast, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 105 days.

(21) Appl. No.: 13/553,861

(22) Filed: Jul. 20, 2012

(65) Prior Publication Data

US 2014/0024916 A1 Jan. 23, 2014

(51) Int. Cl.
*A61B 5/05* (2006.01)
*A61B 5/00* (2006.01)
*A61B 6/00* (2006.01)
*A61B 5/0452* (2006.01)
*A61B 6/03* (2006.01)
*A61B 8/00* (2006.01)
*G01R 33/567* (2006.01)

(52) U.S. Cl.
CPC .............. *A61B 5/7285* (2013.01); *A61B 5/0452* (2013.01); *A61B 5/7289* (2013.01); *A61B 6/483* (2013.01); *A61B 6/5288* (2013.01); *A61B 6/541* (2013.01); *A61B 6/032* (2013.01); *A61B 6/037* (2013.01); *A61B 8/00* (2013.01); *G01R 33/5673* (2013.01)

(58) Field of Classification Search
USPC .......................... 600/413, 514, 509, 526, 528
See application file for complete search history.

(56) References Cited

U.S. PATENT DOCUMENTS

| | | | | |
|---|---|---|---|---|
| 4,240,440 A * | 12/1980 | Groch et al. | .................. | 600/431 |
| 4,245,647 A * | 1/1981 | Randall | .......................... | 600/436 |
| 4,546,777 A * | 10/1985 | Groch et al. | .................. | 600/528 |
| 4,855,910 A * | 8/1989 | Bohning | ........................ | 324/309 |
| 5,781,010 A * | 7/1998 | Kawasaki et al. | ............. | 324/309 |
| 5,803,914 A * | 9/1998 | Ryals et al. | .................... | 600/407 |
| 6,466,640 B1 * | 10/2002 | Taguchi | .......................... | 378/15 |
| 6,674,879 B1 * | 1/2004 | Weisman et al. | ............. | 382/128 |
| 6,713,766 B2 * | 3/2004 | Garrard et al. | ........... | 250/363.02 |
| 6,728,583 B2 * | 4/2004 | Hallett | ............................ | 700/64 |
| 6,771,999 B2 * | 8/2004 | Salla et al. | ..................... | 600/413 |
| 6,900,441 B2 * | 5/2005 | Coles et al. | .................... | 250/369 |
| 7,349,729 B2 * | 3/2008 | Reeder et al. | ................. | 600/410 |
| 7,862,511 B2 * | 1/2011 | Rafter | ........................... | 600/458 |
| 7,931,595 B2 * | 4/2011 | Bendiksen et al. | ........... | 600/458 |
| 8,195,292 B2 * | 6/2012 | Rosenberg et al. | ............... | 607/9 |
| 8,380,284 B2 * | 2/2013 | Saranathan et al. | .......... | 600/413 |
| 8,858,443 B2 * | 10/2014 | Zhang | ........................... | 600/443 |

(Continued)

FOREIGN PATENT DOCUMENTS

| WO | 9502361 A1 | 1/1995 |
|---|---|---|
| WO | 2005046480 A1 | 5/2005 |

OTHER PUBLICATIONS

Germano et al: "Automatic Quantification of Ejection Fraction From Gated Myocardial Perfusion Spect"; Journal of Nuclear Medicine, vol. 36, No. 11, Nov. 1995, pp. 2138-2147.

Zhang et al: "Assessment of Right Ventricular Function for Patients With Rheumatic Mitral Stenosis by 64-Slice Multi-Detector Row Computed Tomography: Comparison With Magnetic Resonance Imaging"; Chinese Medical Journal, 2012, vol. 125, No. 8, pp. 1469-1474.

(Continued)

*Primary Examiner* — Nicholas Evoy (57) ABSTRACT

A method image includes determining an end systolic imaging trigger, acquiring cardiac imaging data including first imaging data corresponding to a first predetermined data acquisition interval surrounding end systole, and post-processing the cardiac imaging data based at least on the end systolic imaging trigger.

13 Claims, 5 Drawing Sheets

(56) References Cited

U.S. PATENT DOCUMENTS

| | | | |
|---|---|---|---|
| 2003/0001097 A1* | 1/2003 | Garrard et al. | 250/363.02 |
| 2003/0004584 A1* | 1/2003 | Hallett | 700/17 |
| 2004/0260188 A1* | 12/2004 | Syed et al. | 600/509 |
| 2005/0102002 A1* | 5/2005 | Salo et al. | 607/17 |
| 2005/0222515 A1* | 10/2005 | Polyshchuk et al. | 600/528 |
| 2006/0155192 A1* | 7/2006 | Bendiksen et al. | 600/458 |
| 2006/0155204 A1* | 7/2006 | Wariar et al. | 600/528 |
| 2007/0016000 A1* | 1/2007 | Prince et al. | 600/410 |
| 2007/0078344 A1* | 4/2007 | Rafter | 600/450 |
| 2007/0167734 A1* | 7/2007 | Saranathan et al. | 600/410 |
| 2008/0004508 A1* | 1/2008 | Sun et al. | 600/300 |
| 2008/0027324 A1* | 1/2008 | Trojanova et al. | 600/454 |
| 2008/0027341 A1* | 1/2008 | Sackner et al. | 600/509 |
| 2008/0039733 A1* | 2/2008 | Unver et al. | 600/528 |
| 2009/0312648 A1* | 12/2009 | Zhang et al. | 600/483 |
| 2010/0081917 A1* | 4/2010 | Zhang et al. | 600/407 |
| 2010/0087746 A1* | 4/2010 | Radzievsky et al. | 600/528 |
| 2010/0210945 A1* | 8/2010 | Zhang | 600/443 |
| 2010/0312116 A1* | 12/2010 | Pernot et al. | 600/453 |
| 2011/0105931 A1* | 5/2011 | Qu et al. | 600/526 |
| 2013/0060149 A1* | 3/2013 | Song et al. | 600/484 |
| 2013/0060150 A1* | 3/2013 | Song et al. | 600/484 |

OTHER PUBLICATIONS

Miller et al: "Measurement of Global and Regional Left Ventricular Function by Cardiac PET"; PET Ventricular Function, vol. 35, No. 6, Jul. 1004, pp. 999-1005.

Simioni et al: "Heart Stroke Volume, Cardiac Output, and Ejection Fraction in 265 Normal Fetus in the Second Half of Gestation Assessed by 4D Ultrasound Using Spatio-Temporal Image Correlation.'" J. Matern Fetal Neonatal Med., Sep. 2011, vol. 24, No. 9, pp. 1159-1167.

Groch: "A New Approach to Physiologic Triggering in Medical Imaging Using Multiple Heart Sounds Alone"; Thesis (Ph.D.) Rush University, College of Nursing, 1994, Dissertation Abstracts Internationsl, vol. 55-02, Section B, p. 0467.

Groch: "A New Heart-Sounds Gating Device for Medical Imaging"; IEEE Transactions on Biomedical Engineering, vol. 39, No. 3, Mar. 1992, pp. 307-310.

Nagel et al: "Magnetic Resonance Real-Time Imaging for the Evaluation of Left Ventricular Function"; Journal of Cardiovascular Magnetic Resonance, vol. 2 (1), 2000, pp. 7-14.

* cited by examiner

MULTI-CARDIAC SOUND GATED IMAGING AND POST-PROCESSING OF IMAGING DATA BASED ON CARDIAC SOUND

The following generally relates to gated imaging and more particularly to gating imaging based on cardiac acoustics corresponding to multiple known phases of the cardiac cycle and post-processing imaging data based on the cardiac acoustics, and is described with particular application to computed tomography (CT). However, the following is also amenable to other imaging modalities such as magnetic resonance imaging (MRI), positron emission tomography (PET), single photon emission computed tomography (SPECT), ultrasound (US), and/or other imaging modality.

Cardiac CT is CT scanning of the heart and has been used to assess the extent of occlusion in the coronary arteries, for example, to diagnose coronary artery disease. For cardiac CT, generally, a contrast agent is administered to a patient and then their heart is scanned to assess the blood flow to their heart muscle. Dose can be reduced by prospectively gating the CT scan with an electrocardiogram (ECG) signal of the patient. For this, the ECG signal is dynamically analyzed and when the R peak of the QRS complex is detected, the CT scanner is activated to acquire data for a predetermined sub-percentage of the R-R interval to image a particular phase of the cardiac cycle (e.g., a "quiet" phase, or a phase with relatively less motion).

Pulse oximetry (POX) has also been used to trigger cardiac CT scanning. Generally, POX waveforms are free of interference from electromagnetic fields and magneto-hydrodynamic effects, and are more robust to the MR environment than the ECG signal. However, the POX trace varies in amplitude and width, and has a latency of approximately three hundred and fifty milliseconds (350 ms) with respect to the R-wave in the ECG. With Cardiac MR, cardiac motion synchronization is commonly performed using vector electrocardiogram (VCG) triggering. In VCG signals, the electrical activity of the heart is represented in four (4) dimensions (x, y, z, and time). The use of both temporal and spatial information inherent in VCG data improves cardiac triggering in the MR environment.

Acoustic Cardiac Triggering (ACT) using a phonocardiogram (PCG) has been used for imaging the heart in high and ultra-high field (greater or equal to three Tesla, $\geq 3$ T) MR, thereby overcoming difficulties in ECG and/or VCG triggering in such environments. The PCG is a recording of the sounds of the heart, including a distinctive sound when the atrioventricular valves close at the beginning of systole. In the MR environment, the PCG can be obtained using a MR stethoscope based on a pressure transducer or using an opto-acoustic microphone. Triggers are generated by detecting the first heart sound, which is caused by the closing of the A-V valves and coincides with end diastole.

In the techniques discussed above, cardiac imaging is performed with respect to an end diastolic trigger only. The other phases of the cardiac cycle are defined by a delay (e.g., as a percent of the R-R interval, in time, etc.) with respect to that trigger. As a result, the time of end systole is unknown at the time of imaging. Consequently, the time of end systole needs to be determined during post-processing, which is necessary for post-processing calculations such as the quantification of functional parameters that depend on the end systolic volume, or wall thickness, e.g. cardiac output (CO), ejection fraction (EJ), wall thickening, etc. Unfortunately, current post-processing approaches use an estimation of end systole which may introduce error into the calculations depending on how far off the estimate is from the actual end systole.

Aspects described herein address the above-referenced problems and others.

In one aspect, a method image includes determining an end systolic imaging trigger, acquiring cardiac imaging data including first imaging data corresponding to a first predetermined data acquisition interval surrounding end systole, and post-processing the cardiac imaging data based at least on the end systolic imaging trigger.

In another aspect, a system includes a cardiac sound detector that detects cardiac sounds for cardiac cycles during an imaging examination procedure, including a first sound corresponding to end diastole and a second sound corresponding to end systole. The system further includes a filter bank that includes filters for distinguishing between different cardiac sounds, including the first and second sounds. The system further includes a trigger generator that generates triggers that gate imaging procedures, including at least an end diastole trigger and an end systole trigger. The system further includes a post-processing system that processes imaging data from an imaging system based on the at least the end diastole trigger and the end systole trigger.

In another aspect, a computer readable storage medium is encoded with computer readable instructions. The computer readable instructions, when executed by a processor, causes the processor to: determine an end systolic imaging trigger and an end diastolic imaging trigger based on detected cardiac sounds during an imaging procedure, and post-process image data based on the end systolic imaging trigger and the end diastolic imaging trigger. The post-processing includes at least one of: 1) automatically visually presenting image data corresponding to at least one of the end systolic imaging trigger and the end diastolic imaging trigger; 2) generating at least one cardiac parameter based on the image data and the at least one of the end systolic imaging trigger and the end diastolic imaging trigger; 3) generating and displaying an image data based movie based on the image data and the at least one of the end systolic imaging trigger and the end diastolic imaging trigger; or 4) simulating image data between the image data corresponding to the end systolic imaging trigger and the image data corresponding to the end diastolic imaging trigger based on the image data and boundary conditions determined based on the end systolic imaging trigger and the end diastolic imaging trigger.

The invention may take form in various components and arrangements of components, and in various steps and arrangements of steps. The drawings are only for purposes of illustrating the preferred embodiments and are not to be construed as limiting the invention.

Figure 1:
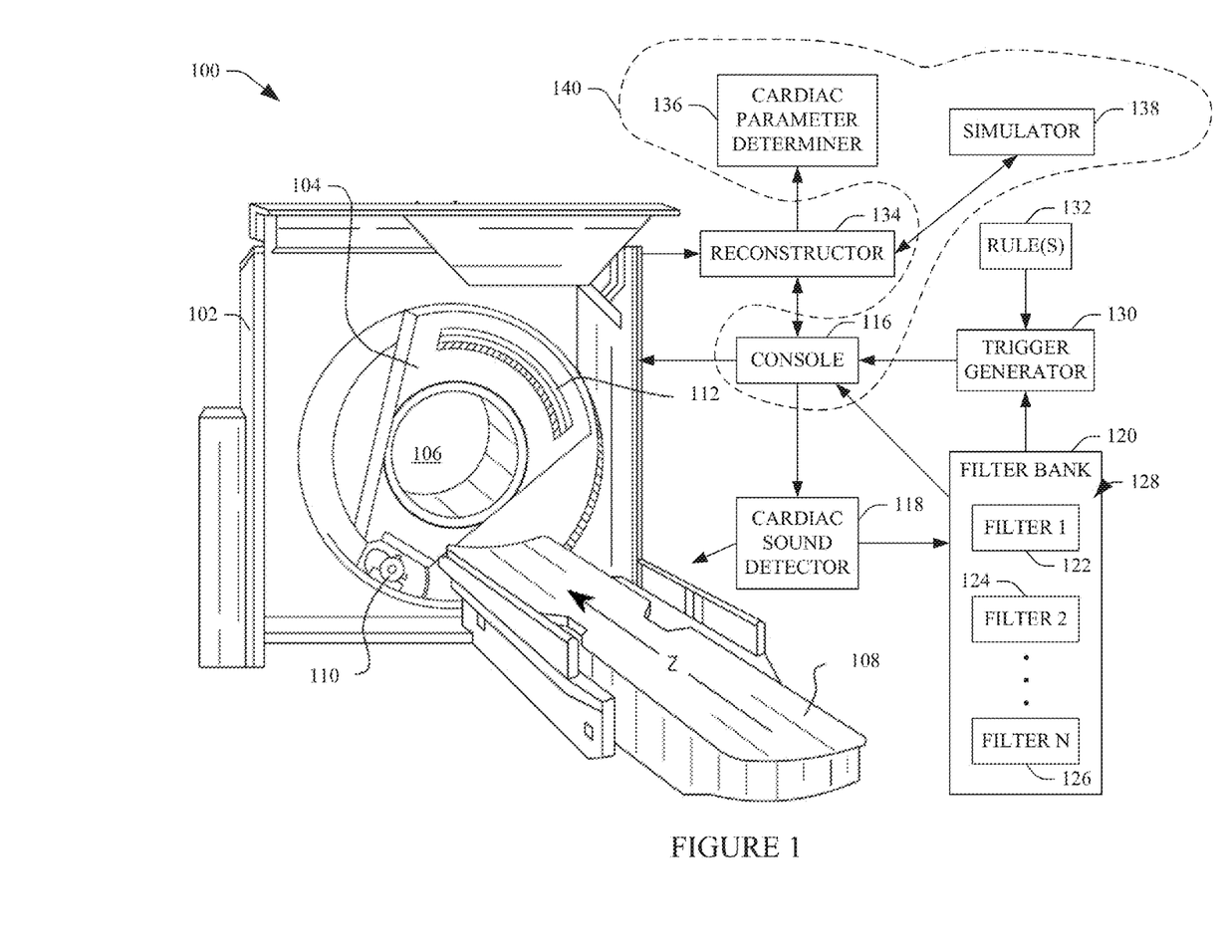
FIG. 1 schematically illustrates an example imaging system configured for cardiac scanning and components for identifying end diastole and end systole and/or triggering scanning and/or processing acquired data based thereon.

Initially referring to FIG. 1, an imaging system 100 is illustrated. The imaging system 100 can include a CT scanner, an MR scanner, a PET scanner, a SPECT scanner, a US scanner, a combined hybrid scanner (e.g., CT/MR scanner), and/or other scanner configured for cardiac imaging. However, for sake of brevity, the following is discussed in connection with a CT scanner.

The imaging system 100 includes a generally stationary gantry 102 and a rotating gantry 104, which is rotatably supported by the stationary gantry 102 and rotates around an examination region 106 about a z-axis. A subject support 108, such as a couch, supports an object or subject in the examination region 106.

A radiation source 110, such as an x-ray tube, is rotatably supported by the rotating gantry 104, rotates with the rotating gantry 104, and emits radiation that traverses the examination region 106. A radiation sensitive detector array 112 subtends an angular arc opposite the radiation source 110 across the examination region 106. The radiation sensitive detector array 112 detects radiation traversing the examination region 106 and generates a signal indicative thereof.

A general-purpose computing system or computer serves as an operator console 116. The console 116 includes a human readable output device such as a monitor and an input device such as a keyboard, mouse, etc. Software resident on the console 116 allows the operator to interact with and/or operate the scanner 100 via a graphical user interface (GUI) or otherwise. Such interaction may include selecting a scan protocol such as a cardiac sound gate imaging protocol, initiating scanning, etc. The console 116 can visually present imaging data based on user input and/or automatically based on triggers, as discussed in greater detail below. Such presentation may include a volume of imaging data or individual images corresponding at least to end systole and/or end diastole, and/or a series of images corresponding at least to end systole and/or end diastole scrolled or looped through in movie-like (or cine) display.

In the illustrated instance, the imaging system 100 is configured for cardiac scanning. In this instance, the imaging system 100 also includes a cardiac sound detector 118. Examples of cardiac sound detector 118 include, but are not limited to, a phonocardiograph and/or a stethoscope, both of which can detect sounds of the heart such as sounds associated with the mitral valves closing at the end of diastole (beginning of systole) and the aortic valve closing at the end of systole (beginning of diastole). The cardiac sound detector 118 may additionally or alternatively include other devices that sense cardiac sounds.

A filter bank 120 includes N filters, a filter 122, a filter 124, . . . , and a filter 126 (collectively referred to herein as filters 128), where N is an integer greater or equal than two. Each of the filters 128 is configured to pass a signal corresponding to a specific cardiac sound and filter out other signals corresponding to other cardiac sounds. Examples of such sounds include, but are not limited to, a closing of the mitral valves, a closing of the aortic valves, murmurs, and/or other cardiac sounds. Such sounds have unique characteristics (e.g., amplitudes, times between sounds, etc.), which are utilized by the filters 128 to differentiate between the sounds.

Figure 2:
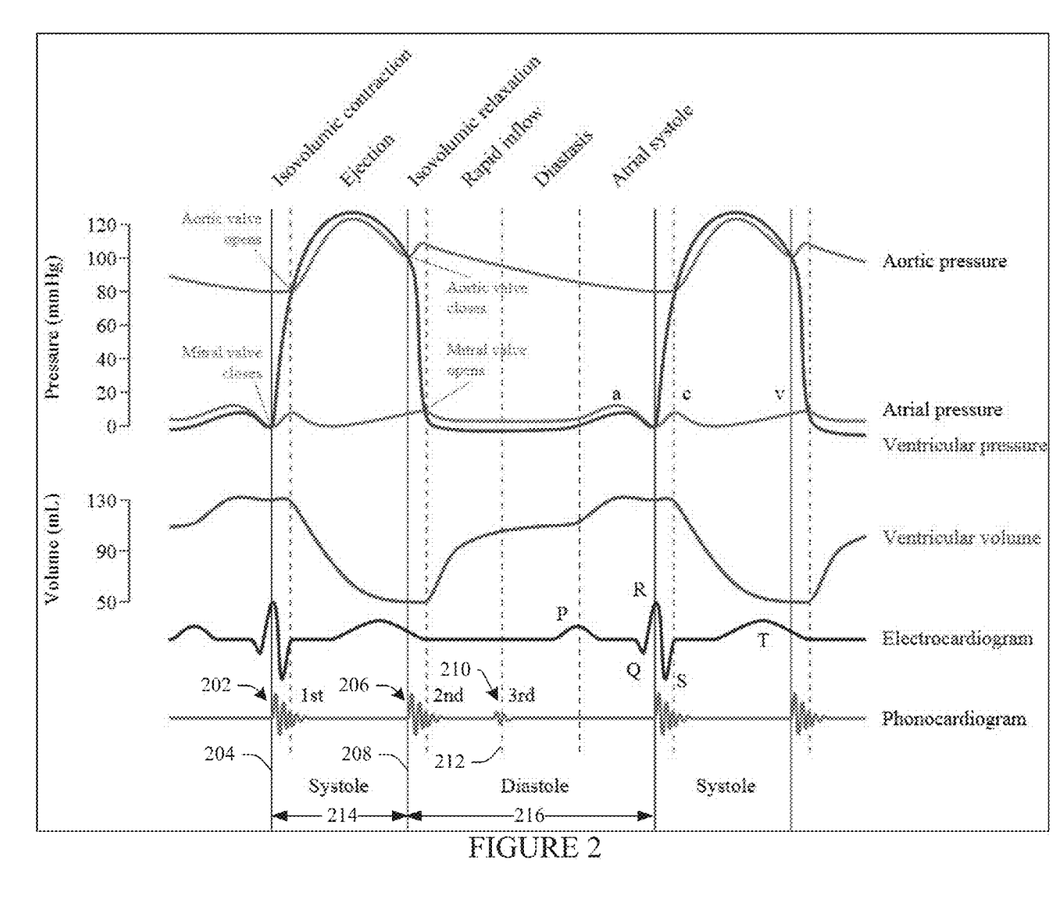
FIG. 2 shows the Wiggers diagram of physiological signals throughout a cardiac cycle.

This is illustrated in the Wiggers Diagram, which is reproduced in FIG. 2. As shown in FIG. 2, a mitral (or end diastole) signal 202 corresponding to a closing of one of the mitral valves 204 (i.e., from the reverberation of blood from the sudden closure of the mitral valve) and an aortic (or end systole) signal 206 corresponding to a closing of one of the aortic valves 208 (i.e., from the reverberation of blood from the sudden closure of the aortic valve) have larger peak amplitudes relative to a signal 210 corresponding to a pathology and the filling of one of the ventricles 212. As such, the filters for the signals 202 and 206 may include amplitude thresholds. In addition, a D-S time 214 between end diastole and end systole is shorter than an S-D time 216 between end systole and end diastole. As such, the filters for the signals 202 and 206 may include time thresholds.

Returning to FIG. 1, a trigger generator 130 receives the signal output by the filter bank 120 and generates and transmits a control signal to the console 116 in response thereto based on one or more rules 132. For example, where the signal from the filter bank 120 is from one the N filters 128 corresponding to the closing of the mitral valve and the one or more rules 132 indicate that data is to be acquired beginning at this event for a predetermined time interval, the trigger generator 130 generates and transmits a data acquisition trigger signal to the console 116. The console 116, in response thereto, acquires data for the predetermined time interval.

Detected signals not corresponding to a cardiac sound of interest are filtered out and not used to invoked data acquisition triggers. In instances in which data is to be acquired at end systole and at end diastole, respectively for time intervals less than the D-S time 214 (FIG. 2) and the S-D time 216 (FIG. 2), the trigger generator 130 generates and transmits corresponding triggers signals to the console 116 upon receiving signals from the filter bank 120 corresponding thereto. An example of a suitable time interval is a time interval in a range of twenty (20) to forty (40) ms. However, other time interval, including shorter and larger time intervals, are contemplated herein.

It is to be appreciated that by detecting both of the signals 202 and 206, respectively corresponding to end diastole and end systole, data acquisition time intervals can be optimized around cardiac phases corresponding thereto, where these cardiac phases are of interest, which may reduce patient dose and improve cardiac systole based parameter determination relative to a configuration in which only the signal corresponding to end diastole is detected and the data acquisition time interval is approximated to be long enough to capture these phases and end systole is determined via post processing of the acquired data. In addition, less data is acquired (optimized about end diastole and end systole), reducing storage demands and/or network load. Of course, the signals 202 and 206 and/or other signals can be used to trigger data acquisition and determine time intervals for other cardiac phases.

Alternatively, the triggers are stored for subsequent processing (as discussed below) and the entire cardiac cycle is scanned.

A reconstructor 134 reconstructs the detector array 112 output signal, generating volumetric image data. In one instance, this includes reconstructing image data corresponding to only a sub-portion of the entire cardiac cycle such as specific phases of the cardiac cycle (e.g., end diastole and end systole) and/or the entire cardiac cycle. In another instance, data acquired over the entire cardiac cycle is reconstructed and the detected signals 202 and 206 (FIG. 2) are employed to identify the reconstructed image data corresponding to end diastole and end systole. The identified cardiac phases can then be extracted from the volume of image data and/or highlighted (e.g., via color, text indicia, etc.) and/or otherwise emphasized in the volume of image data.

An optional cardiac parameter determiner 136 processes the image data output by the reconstructor 134 and determines various cardiac parameters based on the end diastole signal 202 and/or end systole 206. Examples of such parameters include, but are not limited to cardiac output (CO), stroke volume (SV), Ejection Fraction (EJ), end diastolic volume (EDV), and end systolic volume (ESV). These parameters can be calculated from imaging data based on known and/or other approaches. For example, the literature listed in the following paragraph discusses known approaches for calculating one or more of these parameters respectively using CT and MR, SPECT, PET and US imaging data. Approaches discussed in other literature are also contemplated herein.

Zhang et al., "Assessment of Right Ventricular Function for Patients with Rheumatic Mitral Stenosis by 64-Slice Multi-Detector Row Computed Tomography: Comparison with Magnetic Resonance Imaging," Chinese Medical Journal 2012; 125(8): 1469-1474; Germano et al., "Automatic Quantification of Ejection Fraction from Gated Myocardial Perfusion SPECT," The Journal of Nuclear Medicine, Vol. 36, No. 11, November 1995; Miller et al., "Measurement of Global and Regional Left Ventricular Function by Cardiac PET," The Journal of Nuclear Medicine, Vol. 35, No. 6, July 1994; and Simioni et al., "Heart Stroke Volume, Cardiac Output, and Ejection Fraction in 265 Normal Fetus in the Second Half of Gestation Assessed by 4D Ultrasound Using Spatio-Temporal Image Correlation," The Journal of Maternal-Fetal & Neonatal Medicine 2011 September; 24(9): 1159-67.

An optional simulator 138 employs received image data corresponding to end diastole and end systole (e.g., the signals 202 and 206) and simulates images there between for other phases of the heart. In one instance, the simulator 138 employs an anatomical model such as a generic or a patient specific anatomical model and the measured times of end diastole and end systole. For example, left ventricular remodeling after myocardial infarction can be simulated/predicted based on measurements of myocardial strain. The dynamic contractile pattern of the heart can be a crucial parameter in such simulation, which may be described more accurately if measured end diastolic and end systolic timings are available during simulation.

It is to be understood that the filter bank 120, the trigger generator 130, the cardiac parameter determiner 136 and/or the simulator 138 can be implemented by at least one processor that executes at least one computer readable instruction stored in computer readable storage medium, such as physical memory or other non-transitory storage medium. The processor may also execute one or more computer readable instructions carried by a carrier wave, a signal or other transitory medium. As shown in FIG. 1, at least the console 116, the cardiac parameter determiner 136 and the simulator 138 can be considered as part of an overall image data post-processing system 140. However, these components may be part of the same computing device and/or different computing devices.

Figure 3:
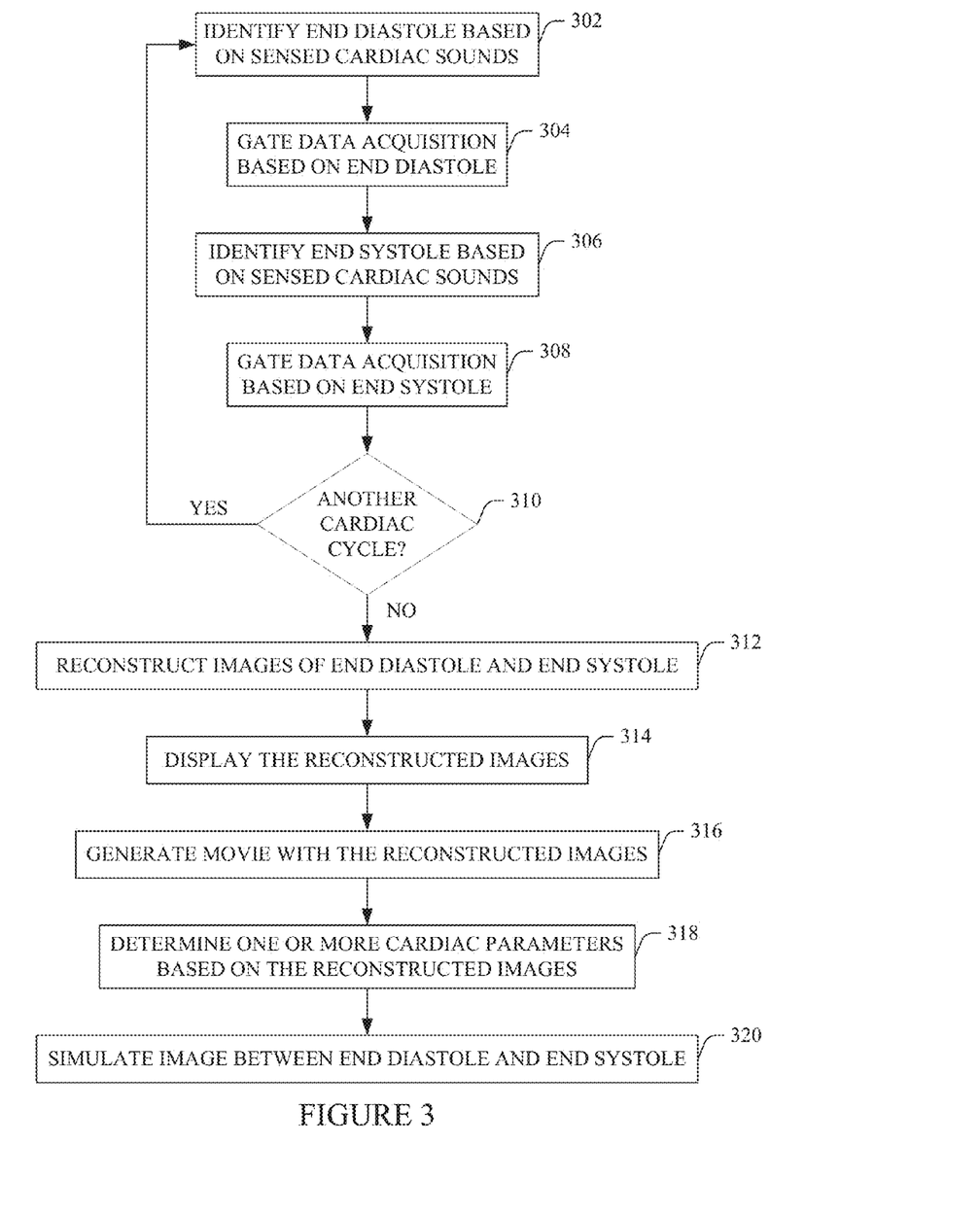
FIG. 3 illustrates an example method for prospectively gating imaging based on cardiac sounds to acquire data at end diastole and end systole
Figure 4:
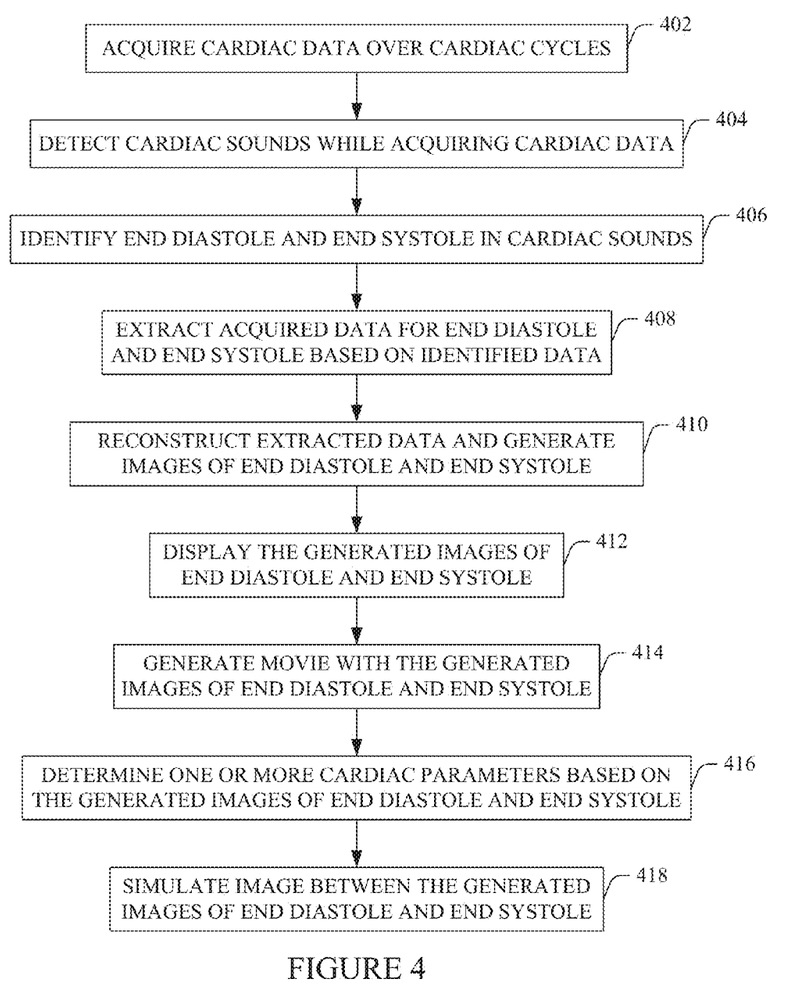
FIG. 4 illustrates an example method for retrospectively gating imaging based on cardiac sounds to extract image data corresponding to end diastole and end systole from a set of volumetric image data.
Figure 5:
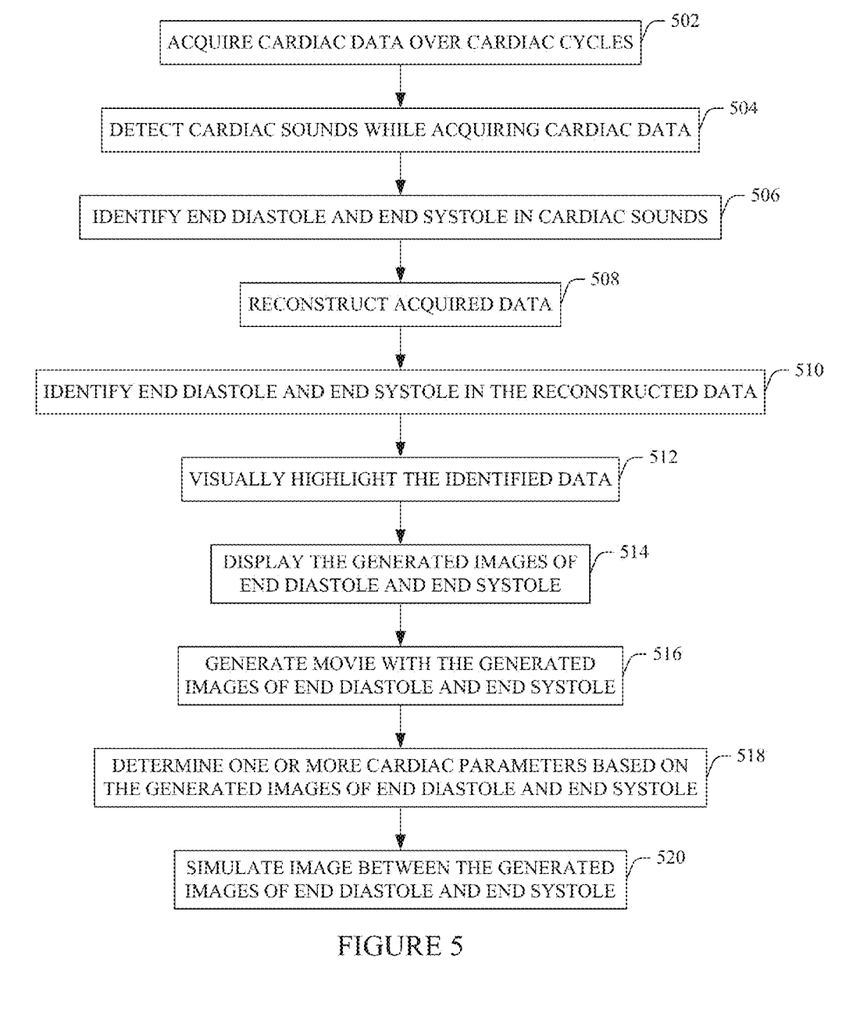
FIG. 5 illustrates an example method for retrospectively gating imaging based on cardiac sounds to extract image data corresponding to end diastole and end systole from a set of volumetric image data.

FIGS. 3, 4 and 5 illustrate example methods for gating imaging. It is to be appreciated that the ordering of the acts in these methods is not limiting. As such, other orderings are contemplated herein. In addition, one or more acts may be omitted and/or one or more additional acts may be included.

Initially referring to FIG. 3, an example method for prospectively gating imaging based on cardiac sounds to acquire data at end diastole and end systole is illustrated.

At 302, while detecting cardiac sounds of a patient during an imaging procedure of the patient, end diastole (or end systole) of a cardiac cycle of the patient is identified based on the detected cardiac sounds.

At 304, data acquisition is gated for a first predetermined time interval in response to identifying end diastole and first data corresponding to end diastole is acquired.

At 306, while detecting the cardiac sounds of the patient during the imaging procedure of the patient, end systole (or end diastole) of the cardiac cycle of the patient is identified based on the detected cardiac sounds.

At 308, data acquisition is gated for a second predetermined time interval in response to identifying end systole and second data corresponding to end systole is acquired.

At 310, it is determined whether data for another cardiac cycle is to be acquired.

If so, acts 302-310 are repeated.

If not, then at 312 the acquired data is reconstructed, generating first volumetric image data corresponding to end diastole and second volumetric image data corresponding to end systole.

At 314, optionally, at least the first volumetric image data corresponding to end diastole and the second volumetric image data corresponding to end systole are displayed.

At 316, optionally, at least the first volumetric image data corresponding to end diastole and the second volumetric image data corresponding to end systole are combined to generate a series of images which are scrolled or looped through in movie-like display.

At 318, optionally, one or more cardiac parameters are determined based at least on the first volumetric image data corresponding to end diastole and the second volumetric image data corresponding to end systole.

At 320, optionally, image data between the first volumetric image data and the second volumetric image data is simulated based on a model for other phases of the cardiac cycle and the first and second volumetric image data.

Turning to FIG. 4, an example method for retrospectively gating imaging based on cardiac sounds to extract image data corresponding to end diastole and end systole from a set of volumetric image data is illustrated.

At 402, cardiac imaging data is acquired while scanning a patient over a plurality of cardiac cycles.

At 404, cardiac sounds of the patient are detected while scanning the patient.

At 406, end diastole and end systole are identified based on the detected cardiac sounds.

At 408, acquired data corresponding to end diastole and end systole is extracted.

At 410, the extracted acquired data is reconstructed, thereby generating volumetric image data corresponding to end diastole and end systole.

At 412, optionally, at least the first volumetric image data corresponding to end diastole and the second volumetric image data corresponding to end systole are displayed.

At 414, optionally, at least the first volumetric image data corresponding to end diastole and the second volumetric image data corresponding to end systole are combined to generate a series of images which are scrolled or looped through in movie-like display.

At 416, optionally, one or more cardiac parameters are determined based at least on the first volumetric image data corresponding to end diastole and the second volumetric image data corresponding to end systole.

At 418, optionally, image data between the first volumetric image data and the second volumetric image data is generated based on a model for other phases of the cardiac cycle and the first and second volumetric image data.

Next at FIG. 5, an example method for retrospectively gating imaging based on cardiac sounds to highlight image data corresponding to end diastole and end systole in a set of volumetric image data is illustrated.

At 502, cardiac imaging data is acquired while scanning a patient over a plurality of cardiac cycles.

At 504, cardiac sounds of the patient are detected while scanning the patient.

At 506, an end diastole phase and an end systole phase are identified based on the detected cardiac sounds.

At 508, the acquired data is reconstructed, thereby generating volumetric image data.

At 510, a subset of volumetric image data corresponding to the end diastole phase and the end systole phase is identified in the volumetric image data.

At 512, the identified data in the volumetric image data corresponding to end diastole and end systole is highlighted.

At 514, optionally, at least the first volumetric image data corresponding to end diastole and the second volumetric image data corresponding to end systole are displayed.

At 516, optionally, at least the first volumetric image data corresponding to end diastole and the second volumetric image data corresponding to end systole are combined to generate a series of images which are scrolled or looped through in movie-like display.

At 518, optionally, one or more cardiac parameters are determined based at least on the first volumetric image data corresponding to end diastole and the second volumetric image data corresponding to end systole.

At 520, optionally, image data between the first volumetric image data and the second volumetric image data is simulated based on a model for other phases of the cardiac cycle and the first and second volumetric image data.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
   determining, via a hardware processor, an end systolic imaging trigger;
   prospectively gating a first scan performed using an imaging system, and gated based at least on the end systolic imaging trigger, wherein first cardiac imaging data is acquired with the prospective gating, by the imaging system during the first scan and the first imaging data corresponds to a first predetermined data acquisition interval surrounding end systole;
   determining, via the hardware processor, an end diastolic imaging trigger;
   prospectively gating a second scan performed using the imaging system, and gated based at least on the diastolic imaging trigger, wherein second cardiac imaging data is acquired with the prospective gating by the imaging system during the second scan and the second imaging data corresponds to a second predetermined data acquisition interval about end diastole; and
   post-processing the first and the second cardiac imaging data.

2. The method of claim 1, wherein only the first cardiac imaging data and the second cardiac imaging data are acquired.

3. The method of claim 1, further comprising:
   acquiring data indicative of cardiac acoustics over at least one cardiac cycle;
   identifying a cardiac sound corresponding to end systole;
   generating the end systolic imaging trigger based thereon; and
   employing the end systolic imaging trigger to gate the first scan and acquire the first cardiac imaging data.

4. The method of claim 3, further comprising:
   identifying another cardiac sound corresponding to end diastole;
   generating the end diastolic imaging trigger based thereon; and
   employing the end diastolic imaging trigger to gate the second scan and acquire the second cardiac imaging data.

5. A method, comprising:
   determining, via a hardware processor, an end systolic imaging trigger;
   gating a first scan performed with an imaging system, via prospectively gating, based at least on the end systolic imaging trigger, wherein first cardiac imaging data is acquired by the imaging system during the first scan and the first imaging data corresponds to a first predetermined data acquisition interval surrounding end systole;
   determining, via the hardware processor, an end diastolic imaging trigger;
   gating a second scan performed with the imaging system, via prospectively gating, based at least on the diastolic imaging trigger, wherein second cardiac imaging data is acquired by the imaging system during the second scan and the second imaging data corresponds to a second predetermined data acquisition interval about end diastole;
   post-processing the first and the second cardiac imaging data based on the end systolic imaging trigger and the end diastolic imaging trigger; and
   simulating imaging data between the first and second imaging data based on an anatomical model of the heart and boundary conditions determined based on the end systolic imaging trigger and the end diastolic imaging trigger.

6. The method of claim 1, further comprising:
   acquiring, with the imaging system and during a scan, third cardiac imaging data for at least three phases of the cardiac cycle, including end diastole and end systole;
   extracting the first cardiac imaging data corresponding to end systole based on the end systolic imaging trigger from the third cardiac imaging data; and
   reconstructing the extracted first imaging data, thereby generating reconstructed imaging data corresponding to end systole.

7. The method claim 6, further comprising:
   reconstructing the third cardiac imaging data, thereby generating reconstructed imaging data of the three or more cardiac phases; and
   highlighting a sub-set of imaging data in the reconstructed imaging data of the three or more cardiac phases corresponding to end systole based on the end systolic imaging trigger.

8. The method of claim 6, further comprising:
   extracting the second cardiac imaging data corresponding to end diastole based on the end diastolic imaging trigger from the third cardiac imaging data; and
   reconstructing the extracted second imaging data, thereby generating reconstructed imaging data corresponding to end diastole.

9. The method of claim 8, further comprising:
   reconstructing the third cardiac imaging data, thereby generating reconstructed imaging data of the three or more cardiac phases; and highlighting a sub-set of imaging data in the reconstructed imaging data of the three or more cardiac phases corresponding to end diastole based on the end diastolic imaging trigger.

10. The method of claim 1, wherein the post-processing includes visually presenting, automatically, imaging data corresponding to end systole based on the end systolic imaging trigger.

11. The method of claim 1, wherein the post-processing includes visually presenting, automatically, imaging data corresponding to end diastole based on the end diastolic imaging trigger.

12. The method of claim 1, wherein the post-processing includes generating and displaying a movie using the imaging data corresponding to end diastole and end systole based on the end diastolic imaging trigger and the end systolic imaging trigger.

13. The method of claim 1, wherein the post-processing includes determining one or more of stroke volume, cardiac output, ejection fraction, end diastolic volume, or end systolic volume based on reconstructed imaging data.

* * * * *